United States Patent [19]

Ohlendorf et al.

[11] 4,279,905
[45] Jul. 21, 1981

[54] 1-BENZOXEPIN-5 (2H)-ONE DERIVATIVES AND PHARMACEUTICAL COMPOSITIONS

[75] Inventors: Heinrich-Wilhelm Ohlendorf, Hanover; Klaus-Ullrich Wolf, Haenigsen; Wilhelm Kaupmann, Hannover-Kirchrode, all of Fed. Rep. of Germany

[73] Assignee: Kali-Chemie Pharma GmbH, Hanover, Fed. Rep. of Germany

[21] Appl. No.: 173,076

[22] Filed: Jul. 28, 1980

[30] Foreign Application Priority Data

Aug. 2, 1979 [DE] Fed. Rep. of Germany ....... 2931398

[51] Int. Cl.$^3$ ................. A61K 31/335; C07D 313/08
[52] U.S. Cl. .................................... 424/246; 548/300; 548/356; 260/326.5 S; 260/326.5 CA; 260/330; 260/333; 260/340.3; 260/340.5 R; 424/248.52; 424/248.56; 424/250; 424/251; 424/267; 424/270; 424/272; 424/273 R; 425/274; 425/275; 425/278; 425/282; 544/3; 544/54; 544/58.7; 544/63; 544/96; 544/147; 544/238; 544/333; 544/376; 546/196; 548/146; 548/214; 548/215; 548/240
[58] Field of Search ............... 260/326.5 S, 326.5 CA, 260/330, 333, 340.5, 340.5 R; 424/246, 248.52, 248.56, 250, 251, 267, 270, 272, 273 R, 274, 275, 278, 282; 544/3, 54, 58.7, 63, 96, 147, 238, 333, 376; 546/196; 548/146, 214, 215, 240, 300, 356

[56] References Cited

U.S. PATENT DOCUMENTS

3,991,082  11/1976  Klutchko et al. ............. 260/333 X
4,153,612  5/1979   McCall ........................ 260/333 X

OTHER PUBLICATIONS

Huckle et al., J. Chem. Soc. (©), 1971, pp. 2252-2260.
Tandon et al., Indian Journal of Chemistry, vol. 13 (1975), pp. 1-8.
Tandon et al., Indian Journal of Chemistry, vol. 15(B), pp. 264-266.
Khanna et al., J. Indian Chem. Soc., vol. 51(1), 1974, pp. 289-303.

*Primary Examiner*—Richard Raymond
*Attorney, Agent, or Firm*—Schwartz, Jeffery, Schwaab, Mack, Blumenthal & Koch

[57] ABSTRACT

Novel, 3-amino-1-benzoxepin-5 (2H)-one derivatives and methods for their production are disclosed. These derivatives correspond to the Formula I:

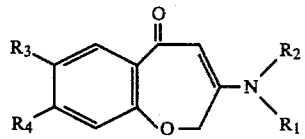

wherein:
$R_1$ and $R_2$ independently of one another are hydrogen,
$C_1$-$C_5$ alkyl,
$C_1$-$C_5$ alkyl substituted with a terminal phenyl, or a phenyl containing one or two halogens, methyl or methoxy groups, a 3,4-methylenedioxy or a 3,4-ethylenedioxy group,
$C_2$-$C_5$ alkyl substituted with terminal hydroxy or methoxy or,
$C_3$-$C_4$ alkenyl; or
one of $R_1$ and $R_2$ are hydrogen or a $C_1$-$C_5$ alkyl and the other is a $C_2$-$C_5$ alkyl substituted with a terminal $NR_5R_6$;
$R_5$ and $R_6$ independently of one another are hydrogen or $C_1$-$C_5$ alkyl; or
$R_5$ and $R_6$ are together a 5 to 7 member ring, or
$R_5$ and $R_6$ are together a 5 to 7 member ring having heterogeneous oxygen, sulfur or nitrogen;
$R_1$ and $R_2$ are together a 5 to 7 member ring, or
$R_1$ and $R_2$ are together a 5 to 7 member ring having heterogeneous oxygen, sulfur or $NR_7$;
$R_7$ is hydrogen, methyl, benzyl or phenyl;
$R_3$ and $R_4$ independently of one another are hydrogen, halogen, $C_1$-$C_4$ alkyl, $C_1$-$C_4$ alkoxy or $C_1$-$C_4$ alkylthio; or
one of $R_3$ and $R_4$ is trifluoromethyl or nitro and the other is hydrogen;

and the acid addition salts thereof. These compounds have a favorable effect on the treatment of spasms of the stomach-intestinal tract and, therefore, constitute the active ingredient of pharmaceutical compositions and methods for the treatment of disorders of the stomach and intestinal tract. Processes for the preparation of the derivatives and their acid addition salts and intermediate products for their preparation are also descrived.

9 Claims, No Drawings

1-BENZOXEPIN-5 (2H)-ONE DERIVATIVES AND PHARMACEUTICAL COMPOSITIONS

BACKGROUND OF THE INVENTION

1. Field of the Invention

The present invention relates to novel and useful 1-benzoxepin-5(2H)-one derivatives and the salts of such derivatives, methods of their production the production of intermediate compounds, the intermediate compounds themselves as well as substances containing pharmaceutically effective amounts of such derivatives. More particularly, the present invention relates to certain pharmaceutically active 1-benzoxepin-5-(2H)-one derivatives, their acid addition salts and intermediate compounds as well as to the process of producing these pharmaceutically active derivatives and acid addition salts and the pharmaceutical compositions themselves as well as to a method of using such compositions in therapy and more particularly, for the treatment of certain gastrointestinal disorders and diseases.

2. Background of the Prior Art

It is known that a considerable number of gastroenterological complaints are caused by functional disturbances. Disorders of the motility, more particularly of the stomach and its sphincters, have been recognized more and more as the cause of various diseases and disorders of the gastrointestinal tract. See, for instance, "Leber, Magen, Darm" (liver, stomach, intestines) Vol. 8 (1978) No. 4, pages 177 to 182 and pages 184 to 190 or, respectively, "Internist" Vol. 20, 1979, pages 10 to 17. More particularly, a pylorus incompetence which is made responsible for the duodeno-gastric reflux, is discussed extensively in connection with a search for the pathologic-physiological causes of various disturbances and disorders of the gastrointestinal tract. See, for instance, "Digestive Diseases" Vol. 21, 1976, No. 2, pages 165 to 173. According to these discussions and publications, the reflux gastritis, the ulcus ventriculi and duodeni, as well as the sense of fullness, nausea, and epigastric pain without anatomically recognizable reasons are caused, or complicated in their course by disorders of the gastric passage.

Heretofore, no satisfactory pharmaceutical agent for treating disorders of the gastrointestinal motility was known.

SUMMARY OF THE INVENTION

It is one object of the present invention to provide novel and useful 1-benzoxepin-5(2H)-one derivatives and their acid addition salts.

Another object of the invention is to provide simple and advantageous processes of producing such novel 1-benzoxepin-5(2H)-one derivatives and their acid addition salts.

Another object of the invention is to provide intermediate compounds for the production of the pharmacologically active 1-benzoxepin-5(2H)-one derivatives.

Still another object of the present invention is to provide compositions containing such 1-benzoxepin-5(2H)-one derivatives and their acid addition salts and, especially, pharmaceutical compositions containing same.

A further object of the present invention is to provide a novel and highly effective method of treating certain gastro-intestinal disorders and diseases by administering such pharmaceutical compositions to patients.

Other objects and advantageous features of the present invention will become apparent as the description proceeds.

In principle, the aim of the present invention is to provide the medical profession with novel 3-amino-1-benzoxepin-5(2H)-one derivatives having valuable pharmacological and therapeutic properties.

Surprisingly, it was found that the novel compounds have a favorable effect upon gastric motility.

Thus, the present invention comprises novel 3-amino-1-benzoxepin-5(2H)-one derivatives of the following Formula I:

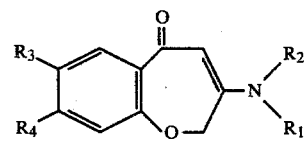

wherein:

$R_1$ and $R_2$ independently of one another are
hydrogen,
$C_1$–$C_5$ alkyl,
$C_1$–$C_5$ alkyl substituted with a terminal phenyl, or a phenyl containing one or two halogens, methyl or methoxy groups, a 3,4-methylenedioxy or a 3,4-ethylenedioxy group,
$C_2$–$C_5$ alkyl substituted with terminal hydroxy or methoxy or,
$C_3$–$C_4$ alkenyl; or
one of $R_1$ and $R_2$ are hydrogen or a $C_1$–$C_5$ alkyl and the other is a $C_2$–$C_5$ alkyl substituted with a terminal $NR_5R_6$;
$R_5$ and $R_6$ independently of one another are hydrogen or $C_1$–$C_5$ alkyl; or
$R_5$ and $R_6$ are together a 5 to 7 member ring, or
$R_5$ and $R_6$ are together a 5 to 7 member ring having heterogeneous oxygen, sulfur or nitrogen
$R_1$ and $R_2$ are together a 5 to 7 member ring, or
$R_1$ and $R_2$ are together a 5 to 7 member ring having heterogeneous oxygen, sulfur or $NR_7$;
$R_7$ is hydrogen, methyl, benzyl or phenyl;
$R_3$ and $R_4$ independently of one another are hydrogen, halogen, $C_1$–$C_4$ alkyl, $C_1$–$C_4$ alkoxy or $C_1$–$C_4$ alkylthio; or
one of $R_3$ and $R_4$ is trifluoromethyl or nitro and the other is hydrogen; and the acid addition salts thereof.

Suitable lower alkyl groups and groups comprising the $R_1$ and $R_2$ moieties include both straight chain and branched chain lower alkyl groups of one to five carbon atoms. For example, methyl, ethyl, propyl, isopropyl, butyl, isobutyl, tert.-butyl, pentyl, isopentyl, neopentyl, allyl, 2-butenyl, 3-butenyl and the like. Preferred are the compounds in which only one of the $R_1$ and $R_2$ groups is a substituted alkyl and the other is a hydrogen or $C_1$–$C_5$ alkyl.

The above-mentioned specific alkyl groups containing one to five carbon atoms are also applicable for $R_5$ and $R_6$.

As examples of substitutions wherein alkyl groups are joined through a nitrogen atom, either directly or through a hetero atom are the following: pyrrolidine, piperidine, azacycloheptane, morpholine, thiomorpholine, piperazine and homo-piperazine wherein it is possible to substitute the nitrogen with methyl, benzyl or phenyl. Preferred are the alkyl groups joined in the form of five and six membered rings.

Substituents $R_3$ and $R_4$ on the phenyl ring may comprise the halogen atoms fluorine, chlorine, bromine and iodine. Especially preferred are fluorine, chlorine and bromine. The $C_1$–$C_4$ alkyl portion of the alkyl, alkoxy or alkylthio groups can be straight chain or branched wherein the methyl groups are especially preferred with multi substitutions on the phenyl ring. Thus, methyl, methoxy, methylthio or methylenedioxy are preferred. If one of the substituents is nitro or trifluoromethyl mono-substitution is preferred.

With substitution of the respective piperazine or homopiperazine and alkyl-$NR_5R_6$, the free bases isolated from the reaction mixture can be converted to their physiologically compatible acid addition salts by treatment with an inorganic or organic acid in the conventional manner. As suitable acids for producing the acid addition salts, hydrochloric acid, hydrobromic acid, sulfuric acid, nitric acid, o-phosphoric acid, maleic acid, cyclohexylamino sulfonic acid, amido sulfonic acid or p-toluene sulfonic acid, are preferred.

The invention also concerns the method of producing the 3-amino-1-benzoxepin-5(2H)-one derivatives of Formula I:

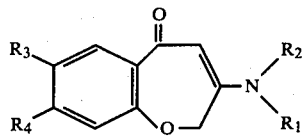
I wherein $R_1$, $R_2$, $R_3$, $R_4$ are defined as above as well as the acid addition salts. The method comprises reacting in an inert solvent the compound of the Formula II:

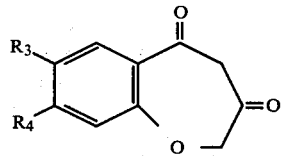
II wherein $R_3$ and $R_4$ are defined as above,
(a) with an amine of the Formula III

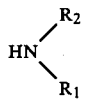
III wherein $R_1$ and $R_2$ are defined as above, or
(b) reacting the 2,3,4,5-tetrahydro-1-benzoxepin-3,5-di-one derivative of Formula II with an acid halide in an inert solvent to form the compound of Formula IV

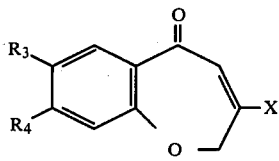
IV wherein $R_3$ and $R_4$ are defined as above and X is chlorine or bromine,
converting these by way of transposition with an amine of the Formula III into the compounds of Formula I, isolating the free base and, as desired, converting to the acid addition salts or
isolating the free base from the acid addition salts.

The transformation of a compound of Formula II or Formula IV with the amine of Formula III is conducted in a conventional manner. For example, the transposition of 2,3,4,5-tetrahydro-1-benzoxepin-3,5-dione derivative of Formula II with the amine of Formula III can preferably be achieved by the addition of catalytic quantity of inorganic and organic acids such as hydrochloric acid, sulfuric acid, p-toluene sulfonic acid or formic acid. As suitable inert solvents chloroform, dichloromethane, benzene and toluene are mentioned. The reaction can be conducted in a temperature range of from 0° to 150° C. The transposition can be carried out in an improvement by removal of the water formed during the reaction in the conventional manner. Use of the compounds of Formula IV in the transposition reaction with the amine of Formula III can be effected in an inert solvent such as chloroform, dichloromethane, dimethylformamide, dioxane and tetrahydrofuran at temperatures between −70° C. and +50° C. The reaction in this instance is conducted in the presence of an organic base such as triethylamine or in excess quantities of the amine compound.

The new compounds of Formula IV can be produced by conventional techniques such that the 2,3,4,5-tetrahydro-1-benzoxepin-3,5-dione derivative of Formula II is reacted with a suitable acid halide. These acid halides may be, for example, a phosphor oxide halide, a phosphoric trihalide, thionyl chloride or especially, oxalylchloride. In the presence of an inert solvent, for example, dichloromethane or dimethylformamide the transposition can be carried out in a temperature range of −20° to 80° C. The reaction product which has been freed from excess acid halide and solvent can be employed for the reaction with the amine of the Formula III.

The 2,3,4,5-tetrahydro-1-benzoxepin-3,5-dione derivatives of Formula II:

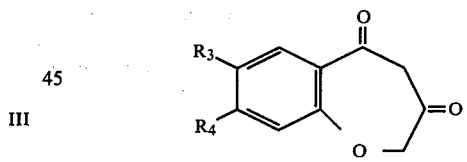
II wherein $R_3$ and $R_4$ are defined as above can be produced by a process comprising reacting the compound the Formula V:

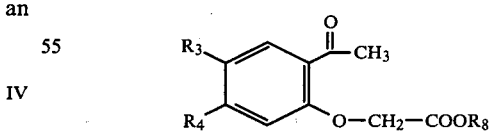
V wherein $R_3$ and $R_4$ are defined as above and $R_8$ is straight chain or branched chain lower molecular alkyl group, preferably a methyl group, in a strong base selected from the group consisting of lithium hydride, sodium hydride, lithium-tert.-butylate and potassium-tert.-butylate in the presence of an inert solvent at a temperature between -70° 1 C. and the boiling point of the solvent. Suitable solvents are, for example, dimethylformamide and tetrahydrofuran.

Ice water can be mixed with the reaction mixture for subsequent treatment permitting the separation of the precipitated compounds of Formula II. The compounds of Formula II can also be separated from the by-products by precipitation from alkali salts, especially lithium salts, with an unpolar solvent, for example, toluene or petroleum ether. The free compounds can be recovered from the salts by means of an inorganic or organic acid, for example, a water solution of hydrochloric acid, sulfuric acid or acetic acid.

It is surprising that with the use of the above-mentioned bases, for example, sodium hydride and lithium-tert.-butylate, the compounds of Formula II can be obtained by closing of the ring structure of the compounds of Formula V. Only benzofuran derivatives can be obtained by cyclization of the 2'-acetylphenoxyacetate with the conventionally used sodium ethylates (see Journal of Organic Chemistry, Vol. 42, 1977, page 4265 as well as Tetrahedron Letters No. 41, 1966, page 4995, paragraph 1). Only the 7-bromo-8-methyl substituted compound is known and the unsubstituted 2,3,4,5-terahydro-1-benzoxepin-3,5-dione which has been isolated, inter alia, upon hydrolysis of 2,3-dihydro-5-hydroxy-3-oxo-1-benzoxepin-4-carboxaldehyde (see Synthesis (1977) page 61 to 63). The substituted 2,3,4,5-tetrahydro-1-benzoxepin-3,5-diones of Formula II are, therefore valuable, new intermediate products and constitute part of the instant invention. For the production of 2,3,4,5-tetrahydro-1-benzoxepin-3,5-dione derivatives of Formula II, necessary 2'-acetylphenoxyacetates can be obtained from 2-hydroxyacetophenones in good yields such that in a simple manner the manufacture of the pharmacologically interesting 3-amino-1-benzoxepin-5(2H)-one derivatives of Formula I is achieved.

DESCRIPTION OF THE PREFERRED EMBODIMENTS

The following examples are to illustrate the present invention. More particularly, the examples illustrate the processes of producing the novel 3-amino-1-benzoxepin-5(2H)-one derivatives of Formula I. These examples are given without in any manner limiting the invention.

EXAMPLE 1

A solution of 88 g (0.5 mole) 2,3,4,5-tetrahydro-1-benzoxepin-3,5-dione and a spatula tip of p-toluene sulfonic acid in 750 ml toluene are mixed while stirring with 44 g (0.5 mole) N,N-dimethylethylenediamine and subsequently stirred to the end of the reaction at room temperature. After concentration of the solution, a product is obtained by filtering off the solution under suction and subsequently recrystallizing from benzene/ligroin. 108 g (88% of the theoretical yield) of 3-($\beta$-dimethylaminoethylamino)-1-benzoxepin-5(2H)-one are obtained. The melting point of this derivative is 100 to 101° C.

EXAMPLE 2

A solution of 17.6 g (0.1 mole) 2,3,4,5-tetrahydro-1-benzoxepin-3,5-dione and a spatula tip of p-toluene sulfonic acid in 200 ml dichloromethane are mixed while stirring with 6 g (0.1 mole) isopropylamine and subsequently stirred to the end of the reaction at room temperature. After concentration of the solution a product is obtained by filtering off under suction and by recrystallizing from butylacetate. 13.5 g (62% of the theoretical yield) of 3-isopropylamino-1-benzoxepin-5(2H)-one are obtained.

EXAMPLE 3

Dimethylamine is introduced while stirring into a boiling solution of 52.8 g (0.3 mole) 2,3,4,5-tetrahydro-1-benzoxepin-3,5-dione and a spatula tip of p-toluene sulfonic acid in 225 ml toluene. The water of reaction is separated by a water separator. After the reaction has ended, the solution is concentrated, the remaining residue is filtered under suction and recrystallized from chloroform/ether. 42 g (69% of the theoretical yield) of 3-dimethylamino-1-benzoxepin-5(2H)-one are obtained. This compound displays a melting point of 136–136° C.

EXAMPLE 4

Methylamine is added with stirring to a boiling solution of 160 g (0.9 mole) 2,3,4,5-tetrahydro-1-benzoxepin-3,5-dione and 1 ml formic acid in 500 ml dichloromethane. The water of reaction is removed by a water separator. After the end of the reaction the solution is cooled with ice, the 3-methylamino-1-benzoxepin-5(2H)-one is filtered under suction and recrystallized from methanol. 140 g (81% of the theoretical yield) of this compound is obtained having a melting point of 176–178° C.

EXAMPLE 5

Ammonia is introduced with stirring to a boiling solution of 70.4 g (0.4 mole) 2,3,4,5-tetrahydro-1-benzoxepin-3,5-dione in 400 ml chloroform. The water of reaction is separated in a water separator. After completion of the reaction, the solution is cooled, the 3-amino-1-benzoxepin-5(2H)-one is filtered under suction and recrystallized. 60.5 g of the product (86% of the theoretical yield) is obtained. The product displays a melting point of 196°–200° C. from chloroform.

EXAMPLE 6

38.1 g (0.3 mole) oxalychloride is added to a solution of 35.2 g (0.2 mole) 2,3,4,5-tetrahydro-1-benzoxepin-3,5-dione in 200 ml dichloromethane. After fourteen hours at room temperature the solvent is removed and the remaining residual oil is distilled. The distillation fraction obtained at 150°–170° C./3 m bar contains as the main product, 3-chloro-1-benzoxepin-5(2H)-one. This is recovered in 100 ml of chloroform. The resulting solution is cooled with ice and mixed by dropwise addition under cooling with an excess of piperidine dissolved in dichloromethane. The solution is stirred to the completion of the reaction at 0° C. and subsequently cooled with ice followed by separation of the organic phase. Thereafter, the organic phase is washed with water, dried and evaporated. The 3-piperidino-1-benzoxepin-5(2H)-one is recrystallized from ether. 19.3 g (40% of the theoretical yield, drawn from 2,3,4,5-tetrahydro-1-benzoxepin-3,5-dione) of the 3-piperidino-1-benzoxepine-5(2H)-one is obtained. The compound displays a melting point 101°–103° C.

EXAMPLE 7

According to the produce of Example 1 through 6, the following compounds can be obtained in similar yields from 2,3,4,5-tetrahydro-1-benzoxepin-3,5-dione and $\beta,\beta$-dimethyl-$\gamma$-dimethylaminopropylamine, n-butylamine, benzylamine, morpholine, $\gamma$-dimethylamino-propylamine, phenethylamine, diethylamine, pyrrolidine, $\beta$-methoxyethylamine, N-benzylpiperazine or tert.-butylamine derivatives of the 1-benzoxepin-3,5-dione:

| | Melting Point °C. |
|---|---|
| 3-(β,β-dimethyl-γ-dimethylamino-propylamino)-1-benzoxepin-5(2H)-one | 111–113 |
| 3-(n-butylamino)-1-benzoxepin-5(2H)-one | 120–122 |
| 3-benzylamino-1-benzoxepin-5(2H)-one | 157–160 |
| 3-morpholino-1-benzoxepin-5(2H)-one | 126–129 |
| 3-(γ-dimethylamino-propylamino)-1-benzoxepin-5(2H)-one | 118–120 |
| 3-phenethylamino-1-benzoxepin-5(2H)-one | 180–182 |
| 3-diethylamino-1-benzoxepin-5(2H)-one | 95–96 |
| 3-pyrrolidino-1-benzoxepin-5(2H)-one | 118–122 |
| 3-(β-methoxyethlamino)-1-benzoxepin-5(2H)-one | 108–110 |
| 3-(N-benzylpiperazino)-1-benzoxepin-5(2H)-one | 132–135 |
| 3-(tert.-butylamino)-1-benzoxepin-5(2H)-one IR (CH$_2$Cl$_2$) 1605 cm$^{-1}$ | oil |

EXAMPLE 8

According to the procedures of the foregoing examples and by known techniques the following:
2,3,4,5-tetrahydro-7-fluoro-1-benzoxepin-3,5-dione,
2,3,4,5-tetrahydro-7-nitro-1-benzoxepin-3,5-dione,
2,3,4,5-tetrahydro-7,8-dichloro-1-benzoxepin-3,5-dione,
2,3,4,5-tetrahydro-7,8-dimethyl-1-benzoxepin-3,5-dione,
2,3,4,5-tetrahydro-7-bromo-1-benzoxepin-3,5-dione,
2,3,4,5-tetrahydro-7-methoxy-1-benzoxepin-3,5-dione,
2,3,4,5-tetrahydro-8-methoxy-1-benzoxepin-3,5-dione,
2,3,4,5-tetrahydro-7-chloro-1-benzoxepin-3,5-dione,
2,3,4,5-tetrahydro-8-chloro-1-benzoxepin-3,5-dione,
2,3,4,5-tetrahydro-7-methyl-1-benzoxepin-3,5-dione,
2,3,4,5-tetrahydro-7-ethyl-1-benzoxepin-3,5-dione,
2,3,4,5-tetrahydro-8-methyl-1-benzoxepin-3,5-dione,
2,3,4,5-tetrahydro-7-chloro-8-methyl-1-benzoxepin-3,5-dione,
2,3,4,5-tetrahydro-8-tert.-butyl-1-benzoxepin-3,5-dione,
and methylamine, dimethylamine or γ-dimethylaminopropylamine derivatives of these compounds are employed to produce the following compounds

| | Melting Point °C. |
|---|---|
| 3-methylamino-7-fluoro-1-benzoxepin-5(2H)-one (. 0.25 H$_2$O) | 216–219 |
| 3-methylamino-7-nitro-1-benzoxepin-5(2H)-one | 200 |
| 3-methylamino-7,8-dichloro-1-benzoxepin-5(2H)-one | 238–241 |
| 3-methylamino-7,8-dimethyl-1-benzoxepin-5(2H)-one | 218–222 |
| 3-methylamino-7-bromo-1-benzoxepin-5(2H)-one | 200–202 |
| 3-methylamino-7-methoxy-1-benzoxepin-5(2H)-one | 169–172 |
| 3-methylamino-8-methoxy-1-benzoxepin-5(2H)-one | 211–214 |
| 3-methylamino-7-chloro-1-benzoxepin-5(2H)-one | 136–198 |
| 3-methylamino-8-chloro-1-benzoxepin-5(2H)-one | 204–208 |
| 3-methylamino-7-methyl-1-benzoxepin-5(2H)-one | 178–180 |
| 3-methylamino-7-ethyl-1-benzoxepin-5(2H)-one | 181–183 |
| 3-dimethylamino-8-chloro-1-benzoxepin-5(2H)-one | 126–129 |
| 3-(γ-dimethylamino-propylamino)-7-chloro-1-benzoxepin-5(2H)-one hydrochloride | 206–208 |
| 3-methylamino-7-chloro-8-methyl-1-benzoxepin-5(2H)-one | 229–234 |
| 3-methylamino-8-methyl-1-benzoxepin-5(2H)-one | 182–184 |
| 3-methylamino-8-tert.-butyl-1-benzoxepin-5(2H)-one | 195–196 |

EXAMPLE 9

30.1 g (1 mole) of sodium hydride (80% in oil) is added at −20° C. in small portions to a cooled solution of 242 g (1 mole) (2'-acetyl-4'-chloro) phenoxyacetic acid-methyl ether in 300 ml dimethylformamide. The addition proceeds such that the temperature is not allowed to rise above −10° C. Subsequently, after stirring for 45 minutes at −15° C., the solution is carefully poured into ice water and extracted with toluene. After acidification of the water phase, the precipitated product is filtered under suction and recrystallized from cyclohexane/toluene. 126 g of 2,3,4,5-tetrahydro-7-chloro-1-benzoxepin-3,5-dione are obtained. This compound displays a melting point of 131°–134° C. The yield is 60% of the theoretical yield.

EXAMPLE 10

8.8 g (0.11 mole) lithium-tert.-butylate in 50 ml dry tetrahydrofuran under cooling is added to a solution of 28.7 g (0.1 mole) (2'-acetyl-4'-bromo) phenoxyacetic acid methyl ester in 150 ml dry tetrahydrofuran. The addition proceeds so that the temperature is maintained between 25° to 35° C. Subsequently, the suspension is poured into 400 ml petrolether and the precipitated lithium salt of 2,3,4,5-tetrahydro-7-bromo-1-benzoxepin-3,5-dione is filtered under suction. These salts are poured into a mixture of 150 ml of water and 11 ml of hydrochloric acid (32%). The precipitated product is filtered under suction, dissolved in dichloromethane, washed in a saturated sodium chloride solution, dried over sodium sulfate, evaporated and recrystallized from cyclohexane. 11.7 g (46% of the theoretical yield) of 2,3,4,5-tetrahydro-7-bromo-1-benzoxepin-3,5-dione are obtained. The compound displays a melting point of 110°–112° C.

EXAMPLE 11

According to the procedure defined in Examples 9 and 10, the following compound can be subjected to treatment with sodium hydride and lithium-tert.-butylate respectively:
(2'-acetyl-4'-methyl)-phenoxyacetic acid-methylester,
(2'-acetyl-5'-methyl)-phenoxyacetic acid-methylester,
(2'-acetyl-5'-chloro)-phenoxyacetic acid-methylester,
(2'-acetyl-4'-fluoro)-phenoxyacetic acid-methylester,
(2'-acetyl-4'-methoxy)-phenoxyacetic acid-methylester,
(2'-acetyl-5'-methoxy)-phenoxyacetic acid-methylester,
(2'-acetyl-4',5'-dichloro)-phenoxyacetic acid-methylester,
(2'-acetyl-4'-chloro-5'-methyl)-phenoxyacetic acid-methylester,
(2'-acetyl-4',5'dimethyl)-phenoxyacetic acid-methylester,
(2'-acetyl-5'-tert.-butyl)-phenoxyacetic acid-methylester,
(2'-acetyl-4'-ethyl)-phenoxyacetic acid-methylester,
2'-acetyl-phenoxyacetic acid-methylester.
Upon such treatment, the following compounds are obtained in yields similar to that of Examples 9 and 10:

| | Melting Point °C. |
|---|---|
| 2,3,4,5-tetrahydro-7-methyl-1-benzoxepin-3,5-dione | 124–127 |
| 2,3,4,5-tetrahydro-8-methyl-1-benzoxepin-3,5-dione | 97–98 |
| 2,3,4,5-tetrahydro-8-chloro-1-benzoxepin-3,5-dione | 152–154 |
| 2,3,4,5-tetrahydro-7-fluoro-1-benzoxepin-3,5-dione | 138–140 |
| 2,3,4,5-tetrahydro-7-methoxy-1-benzoxepin- | |

-continued

| | Melting Point °C. |
|---|---|
| 3,5-dione | 101–102 |
| 2,3,4,5-tetrahydro-8-methoxy-1-benzoxepin-3,5-dione | 125–127 |
| 2,3,4,5-tetrahydro-7,8-dichloro-1-benzoxepin-3,5-dione | 168–170 |
| 2,3,4,5-tetrahydro-7-chloro-8-methyl-1-benzoxepin-3,5-dione | 172–174 |
| 2,3,4,5-tetrahydro-7,8-dimethyl-1-benzoxepin-3,5-dione | 117–118 |
| 2,3,4,5-tetrahydro-8-tert.-butyl-1-benzoxepin-3,5-dione IR(CH$_2$Cl$_2$):1676, 1738 cm$^{-1}$ | oil |
| 2,3,4,5-tetrahydro-7-ethyl-1-benzoxepin-3,5-dione | 74–75 |
| 2,3,4,5-tetrahydro-1-benzoxepin-3,5-dione | 83–86 |
| 2,3,4,5-tetrahydro-7-nitro-1-benzoxepin-3,5-dione | 138–139 |

UTILITY AND TESTS

As stated above, it is an important feature of the present invention to provide the medical profession with novel and highly effective therapeutic agents for restoring physiological motility and unimpeded passage of food through the stomach.

The new compounds and their acid addition salts provide these results. All of them show the retarding and regulating effect with spasms of the smooth musculature in the stomach intestinal canal.

Painful abdominal sicknesses are frequently brought about by spasms in the gastrointestinal canal musculature. The treatment of these spasms are, therefore, the objectives of the numerous spasmolytic working medicaments. Above all, the parasympathicolytica have applied already for many years. The unsatisfactory selectivity of their activity makes their application only suitable within narrow parameters. Above all, undesirable side effects such as dryness of the mouth, impairment of vision and fluid retention prohibit the application of the previously known medicaments in sufficiently high doses.

It has now been surprisingly found that the 3-amino-1-benzoxepin-5(2H)-one derivatives of Formula I produce a specific desired retarding and regulating effect without the chemical or pharmacological disadvantages of the above-mentioned side effects.

DESCRIPTION OF THE PHARMACOLOGICAL TEST METHODS

1. Determination of Acute Toxicity

The acute seven-day toxicity is determined by intraperitoneal administration of a single dose of the respective compound to a fasting white NMRI mouse. The LD$_{50}$-values are calculated via electronic data processing by a probit analysis as described in the book "Grundbegriffe der Biometrie" (Basic Biometrical Definitions) by L. Cavalli-Sforza, page 153 et seq., published by Gustav Fischer Verlag, Stuttgart, 1964.

2. Testing of the Gastric Peristalsis

To determine the functioning of the gastric peristalsis, rats weighing about 200 g are narcotized by means of ketamine hydrochloride and xylazine. A catheter is introduced into the Vena jugularis of the narcotized rats and a tracheal catheter into the trachea. A stomach probe is inserted into their stomach and tied thereto. The probe is connected via a three-way cock with a Statham pressure imparting device (P 23 DB). The stomach is sealed off by a ligature at the pylorus and at the cardia. The stomach is filled with 3 ml of a 0.9% aqueous sodium chloride solution. The pressure waves produced by the stomach are continuously registered by a suitable recording device such by a Watanabe Multicorder (MC 641).

In conducting the test, a control value is obtained by inducing a stimulation of the stomach through a lengthy intravenous infusion of 50 mg/kg/h of bariumchloride and the amplitude and frequency of resultant pressure waves are measured. Subsequently, in order to determine the pharmacological effects, the compounds to be tested are dissolved in physiological sodium chloride solution or are suspended in Tylose MH 50 solution. The solutions or suspensions are then administered intraperitoneally to the rats in a dose of 20 mg/kg. The amplitudes and frequencies of the pressure wave-like movements of the stomach as they occur with the test solution and after administration of the compound to be tested, are compared.

Shortly after administration of the compounds according to the present invention evaluation of the test results shows that the peristaltic movements of the stomach are reduced, which is manifested by a significant reduction in the amplitudes.

The frequency is varied only in small extend as shown in the table which follows. The low toxicity of the substances ensure a good compatibility of the same. A further advantage is the observed rapid onset of activity produced by the novel substances.

The following 3-amino-1-benzoxepin-5(2H)-one compounds were tested according to these methods:
(A) 3-methylamino-1-benzoxepin-5(2H)-one
(B) 3-methylamino-8-chloro-1-benzoxepin-5(2H)-one
(C) 3-isopropylamino-1-benzoxepin-5(2H)-one
(D) 3-amino-1-benzoxepin-5(2H)-one
(E) 3-(n-butylamino)-1-benzoxepin-5(2H)-one
(F) 3-phenethylamino-1-benzoxepin-5(2H)-one
(G) 3-(N-benzylpiperazino)-1-benzoxepin-5(2H)-one
(H) 3-morpholino-1-benzoxepin-5(2H)-one
(I) 3-($\beta$-methoxyethylamino)-1-benzoxepin-5(2H)-one
(K) 3-methylamino-8-methyl-1-benzoxepin-5(2H)-one
(L) 3-methylamino-7-methyl-1-benzoxepin-5(2H)-one
(M) 3-methylamino-8-tert.-butyl-1-benzoxepin-5(2H)-one
(N) 3-methylamino-7-chloro-1-benzoxepin-5(2H)-one
(O) 3-methylamino-7-fluoro-1-benzoxepin-5(2H)-one

TABLE
MEASUREMENT OF THE GASTRIC PRESSURE

| Compound Tested | Factor of the Increase in Amplitude | Frequency Decrease in % | LP$_{50}$ i.p. (mg/kg)* |
|---|---|---|---|
| A | 56 | −18 | 664 |
| B | 58 | −16 | 450 |
| C | 32 | −2 | 544 |
| D | 45 | −12 | 544 |
| E | 26 | +36 | 442 |
| F | 29 | −7 | n.b. |
| G | 31 | +10 | 634 |
| H | 12 | +17 | 650 |
| I | 46 | +11 | n.b. |
| K | 55 | +4 | n.b. |
| L | 75 | +15 | n.b. |
| M | 72 | +10 | n.b. |
| N | 46 | −1 | n.b. |
| O | 37 | +1 | n.b. |

*n.b. indicates test results are not known.

The pharmacologically observed effects clearly indicate that the compounds according to the present invention provide a favorable influence over the various spastic conditions in the stomach-intestinal canal as well as the other components of the digestive system.

Suitable pharmaceutical preparations according to the present invention contain, as effective agents, the 3-amino-1-benzoxepin-5(2H)-one derivatives of Formula I or their pharmacologically compatible acid addition salts in combination with conventional pharmaceutically acceptable excipients, such as carrier materials and/or diluents. The resulting pharmaceutical preparations can be administered orally or parenterally. Suitable preparations are in the form of tablets, capsules, lozenges, sirups, dry powders, injectable or infusible solutions or suspensions. They can also be prepared and administered in the form of suppositories. The preferred preparations are those which can be orally administered.

The dosage to be administered of the pharmaceutical compounds according to the present invention is dependent on various factors, such as the kind and the seriousness of the disease or the compound to be administered. In general a single dose of between 1 mg and 50 mg and preferably between 2 mg and 20 mg, administered orally, is sufficient to achieve satisfactory results.

The following example illustrates the preparation of an orally administrable composition without, however, being limited thereto.

EXAMPLE 12

Capsules containing 3-methylamino-1-benzoxepin-5-(2H)-one as the active compound.

Each capsule contains an intimate mixture of the following ingredients:

| Pharmacologically Active Compound | 10 mg |
| --- | --- |
| Lactose | 65 mg |
| Dried Corn Starch | 40 mg |
| Soluble Starch | 4 mg |
| Magnesium stearate | 1 mg |
| Total Content of Each Capsule | 120 mg |

Production Method:

The pharmacologically active compound is mixed with the lactose and dried corn starch. The resultant mixture is thoroughly wetted with a 15% aqueous solution of the soluble starch and granulated. The damp mass is passed through a 1.6 mm sieve, dried at 40° C. and finally passed through a 1.0 mm sieve. The resulting mixture is encapsuled in amounts of 120 mg after the mixing of the granulates with magnesium stearate. In this fashion, each capsule contains 10 mg of the pharmacologically active compound.

Of course, many changes and variations in the process of producing the compound of Formula I according to the present invention and of their acid addition salts, in the reactants and solvents used, in the reaction conditions, temperature, pressure and duration, in the manner of working up the reaction mixture and of isolating and purifying the resulting reaction products, in the preparation of pharmaceutical compositions containing said 3-amino-1-benzoxepin-5(2H)-one derivatives and their acid addition salts, in the method of administering said pharmaceutical compositions for the treatment of motility disorders of the gastrointestinal tract, and the like may be made by those skilled in the art in accordance with the principles set forth herein and in the claims annexed hereto.

What is claimed is:

1. 3-amino-1-benzoxepin-5(2H)-one derivatives of the following Formula I

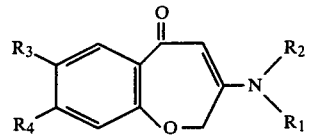

wherein:

$R_1$ and $R_2$ independently of one another are
 hydrogen,
 $C_1$–$C_5$ alkyl,
 $C_1$–$C_5$ alkyl substituted with a terminal phenyl, or a phenyl containing one or two halogens, methyl or methoxy groups, a 3,4-methylenedioxy or a 3,4-ethylenedioxy group,
 $C_2$–$C_5$ alkyl substituted with terminal hydroxy or methoxy or,
 $C_3$–$C_4$ alkenyl; or
one of $R_1$ and $R_2$ are hydrogen or a $C_1$–$C_5$ alkyl and the other is a $C_2$–$C_5$ alkyl substituted with a terminal $NR_5R_6$;
$R_5$ and $R_6$ independently of one another are hydrogen or $C_1$–$C_5$ alkyl; or
$R_5$ and $R_6$ are together a 5 to 7 member ring, or
$R_5$ and $R_6$ are together a 5 to 7 member ring having heterogeneous oxygen, sulfur or nitrogen;
$R_1$ and $R_2$ are together a 5 to 7 member ring, or
$R_1$ and $R_2$ are together a 5 to 7 member ring having heterogeneous oxygen, sulfur or $NR_7$;
$R_7$ is hydrogen, methyl, benzyl or phenyl;
$R_3$ and $R_4$ independently of one another are hydrogen, halogen, $C_1$–$C_4$ alkyl, $C_1$–$C_4$ alkoxy or $C_1$–$C_4$ alkylthio; or
one of $R_3$ and $R_4$ is trifluoromethyl or nitro and the other is hydrogen;
and the acid addition salts thereof.

2. The 3-amino-1-benzoxepin-5(2H)-one derivative of claim 1 comprising 3-A-1-benzoxepin-5(2H)-one wherein A is selected from the group consisting of amino, methylamino, isopropylamino, n-butylamino, tert-butylamino, benzylamino, phenethylamino, diethylamino, pyrrolidino, piperidino, morpholino, n-benzyl-piperazino, β-dimethylamino-ethylamino, β,β-dimethyl-γ-dimethylaminopropylamino and β-methoxyethylamino.

3. The 3-amino-1-benzoxepin-5(2H)-one derivative of claim 1 comprising 3-methylamino-7-B-1-benzoxepin-5(2H)-one wherein B is selected from the group consisting of chloro, bromo, methyl, ethyl and methoxy.

4. The 3-amino-1-benzoxepin-5(2H)-one derivative of claim 1 comprising 3-methylamino-8-C-1-benzoxepin-5(2H)-one wherein C is selected from the group consisting of chloro, methyl, tert.-butyl and methoxy.

5. The 3-amino-1-benzoxepin-5-(2H)-one derivative of claim 1 comprising 3-methylamino-7-B-8-C-1-benzoxepin-5(2H)-one wherein B and C are the same or are different and are selected from the group consisting of chloro and methyl.

6. The 3-amino-1-benzoxepin-5(2H)-one derivative of claim 1 comprising 3-γ-dimethylaminopropylamino-7-B-1-benzoxepin-5(2H)-one wherein B is selected from the group consisting of hydrogen and chloro.

7. The 3-amino-1-benzoxepin-5(2H)-one derivative of claim 1 comprising 3-dimethylamino-8-C-1-benzoxepin- 5(2H)-one wherein C is selected from the group consisting of hydrogen and chlorine.

8. A pharmaceutical composition comprising an effective amount of the 3-amino-1-benzoxepin-5(2H)-one derivative of claim 1 and a pharmaceutically acceptable excipient.

9. A method of treating motility disorders of the gastro-intestinal tract comprising administering an effective amount of 3-amino-1-benzoxepin-5(2H)-one derivative of claim 1.

* * * * *

UNITED STATES PATENT AND TRADEMARK OFFICE
CERTIFICATE OF CORRECTION

PATENT NO. : 4,279,905

DATED : July 21, 1981

INVENTOR(S) : Ohlendorf et al

It is certified that error appears in the above—identified patent and that said Letters Patent is hereby corrected as shown below:

ON THE TITLE PAGE, INFORMATION AT COLUMN 1, at [75] INVENTORS, kindly correct the same as follows:

At line 2, change "Hanover" to read --Hannover--;

At line 4, before "all of Fed." insert the name of the following omitted inventor:

--Henning Heinemann, Hannover--.

Signed and Sealed this

Thirtieth Day of March 1982

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,279,905

DATED : July 21, 1981

INVENTOR(S) : Ohlendorf et al

It is certified that error appears in the above—identified patent and that said Letters Patent is hereby corrected as shown below:

Column 10, in the table, cancel "Factor of the Increase in Amplitude" and substitute --Decrease in Amplitude in %--.

Column 10, in the table, cancel "Frequency Decrease" and substitute --Frequency Change--.

Column 10, in the table, cancel "$LP_{50}$" and substitute --$LD_{50}$--.

Signed and Sealed this

Seventh Day of December 1982

[SEAL]

Attest:

GERALD J. MOSSINGHOFF

Attesting Officer

Commissioner of Patents and Trademarks